(12) United States Patent
O'Brien et al.

(10) Patent No.: US 10,175,188 B2
(45) Date of Patent: Jan. 8, 2019

(54) TRENCH BASED CAPACITIVE HUMIDITY SENSOR

(71) Applicant: Robert Bosch GmbH, Stuttgart (DE)

(72) Inventors: Gary O'Brien, Palo Alto, CA (US); Ando Feyh, Palo Alto, CA (US); Andrew Graham, Redwood City, CA (US); Ashwin Samarao, Mountain View, CA (US); Gary Yama, Mountain View, CA (US)

(73) Assignee: Robert Bosch GmbH, Stuttgart (DE)

( * ) Notice: Subject to any disclaimer, the term of this patent is extended or adjusted under 35 U.S.C. 154(b) by 697 days.

(21) Appl. No.: 13/832,904

(22) Filed: Mar. 15, 2013

(65) Prior Publication Data
US 2017/0082567 A1     Mar. 23, 2017

(51) Int. Cl.
*G01N 27/22* (2006.01)
*B81B 7/00* (2006.01)

(52) U.S. Cl.
CPC ......... *G01N 27/223* (2013.01); *B81B 7/0006* (2013.01); *G01N 27/225* (2013.01); *B81B 2201/0292* (2013.01)

(58) Field of Classification Search
CPC ............. G01N 27/223; B81B 7/0006; B81B 2201/0292
USPC ........................................................ 257/414
See application file for complete search history.

(56) References Cited

U.S. PATENT DOCUMENTS

| | | | |
|---|---|---|---|
| 3,826,979 A | 7/1974 | Steinmann | |
| 6,445,565 B1 | 9/2002 | Toyoda et al. | |
| 6,633,172 B1 | 10/2003 | Doemens et al. | |
| 8,079,248 B2 | 12/2011 | Hoofman et al. | |
| 8,234,773 B2 | 8/2012 | Bedair et al. | |
| 2002/0036507 A1 | 3/2002 | Kiesewetter et al. | |
| 2002/0109959 A1* | 8/2002 | Toyoda | G01N 27/225 361/311 |

(Continued)

FOREIGN PATENT DOCUMENTS

| EP | 2508874 A1 | 10/2012 |
|---|---|---|
| WO | 0142776 A1 | 6/2001 |

OTHER PUBLICATIONS

Supplementary European Search Report corresponding to European Application No. 14767515 (10 pages).

(Continued)

*Primary Examiner* — Marc Armand
*Assistant Examiner* — Sue Tang
(74) *Attorney, Agent, or Firm* — Maginot Moore & Beck LLP

(57) ABSTRACT

A trenched base capacitive humidity sensor includes a plurality of trenches formed in a conductive layer, such as polysilicon or metal, on a substrate. The trenches are arranged parallel to the each other and partition the conductive layer into a plurality of trenched silicon electrodes. At least two trenched silicon electrodes are configured to form a capacitive humidity sensor. The trenches that define the trenched silicon electrodes can be filled partially (e.g., sidewall coverage) or completely with polyimide (PI) or silicon nitride (SiN). A polyimide layer may also be provided on the conductive layer over the trenches and trenched electrodes. The trenches and the trenched silicon electrodes may have different widths to enable different sensor characteristics in the same structure.

7 Claims, 7 Drawing Sheets

(56) References Cited

U.S. PATENT DOCUMENTS

| | | | |
|---|---|---|---|
| 2003/0094045 A1* | 5/2003 | Hamamoto | G01N 19/10 |
| | | | 73/335.04 |
| 2003/0179805 A1 | 9/2003 | Hamamoto et al. | |
| 2004/0080325 A1* | 4/2004 | Ogura | G01N 27/225 |
| | | | 324/664 |
| 2005/0087620 A1 | 4/2005 | Bowers et al. | |
| 2006/0048572 A1* | 3/2006 | Isogai | G01N 27/223 |
| | | | 73/335.04 |
| 2006/0096371 A1 | 5/2006 | Isogai et al. | |
| 2008/0238449 A1* | 10/2008 | Shizu | G01N 33/2852 |
| | | | 324/689 |
| 2010/0314021 A1 | 12/2010 | Zadeh | |
| 2012/0256236 A1 | 10/2012 | Cummins | |

OTHER PUBLICATIONS

International Search Report and Written Opinion corresponding to PCT Application No. PCT/US2014/022205, dated Jun. 24, 2014 (12 pages).

* cited by examiner

TRENCH BASED CAPACITIVE HUMIDITY SENSOR

TECHNICAL FIELD

This disclosure relates generally to semiconductor devices and particularly to microelectromechanical system (MEMS) humidity sensors.

BACKGROUND

Humidity sensors are widely used in various fields to measure the amount of water vapor present in the air of a particular environment. Humidity sensors are often configured as capacitive sensor devices that use capacitance to measure humidity. Capacitive humidity sensors typically include a pair of electrodes separated by a dielectric material. The dielectric layer is formed of a material, such as polymer that is configured to absorb and retain water molecules at concentrations that are proportional to the ambient humidity. The water molecules alter the dielectric constant of the polymer resulting in a change in capacitance between the two electrodes. Humidity can therefore be determined by measuring the capacitance between the two electrodes and correlating the measured capacitance to a corresponding humidity value.

Previously known capacitive humidity sensors often utilize flat, thin interdigital electrodes provided on a surface of a substrate and covered by a polyimide film for capacitance measurement. While such sensors are effective for measuring humidity, they can have a rather large footprint on the surface of the substrate which limits the ability to incorporate humidity sensors into other devices without increasing the size of the device. In addition, such sensors are generally not capable of being efficiently integrated into CMOS processing. As a result, separate chips and separate processing steps are typically required to fabricate capacitive humidity sensors, and special packaging methods are required to incorporate them into other devices.

DETAILED DESCRIPTION

Figure 1:
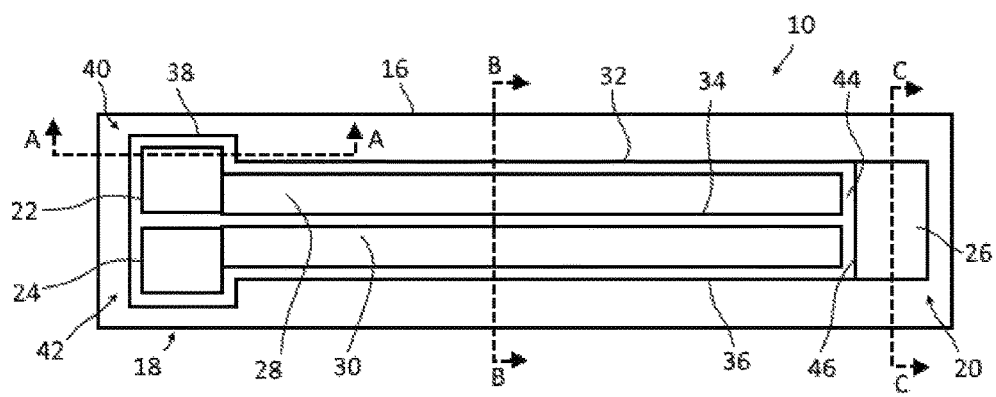
FIG. 1 depicts a top schematic view of an embodiment of a trench based capacitive humidity sensor in accordance with the present disclosure.

For the purposes of promoting an understanding of the principles of the disclosure, reference will now be made to the embodiments illustrated in the drawings and described in the following written specification. It is understood that no limitation to the scope of the disclosure is thereby intended. It is further understood that the present disclosure includes any alterations and modifications to the illustrated embodiments and includes further applications of the principles of the disclosure as would normally occur to one of ordinary skill in the art to which this disclosure pertains.

The present disclosure is directed to a trench based capacitive humidity sensor implemented by a plurality of trenches formed in a conductive layer, such as polysilicon or metal, on a substrate. The trenches are arranged parallel to the each other and partition the conductive layer into a plurality of trenched silicon electrodes. At least two trenched silicon electrodes are configured to form a capacitive humidity sensor. The trenches that define the trenched silicon electrodes can be filled partially (e.g., sidewall coverage) or completely with polyimide (PI) or silicon nitride (SiN). A polyimide layer may also be provided on the conductive layer over the trenches and trenched electrodes. The trenches and the trenched silicon electrodes may have different widths to enable different sensor characteristics in the same structure.

Figure 2A:
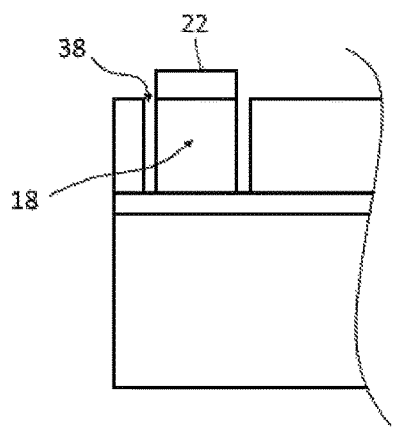
FIG. 2A is a schematic cross-sectional view of the humidity sensor of FIG. 1 taken along line A-A.
Figure 2B:
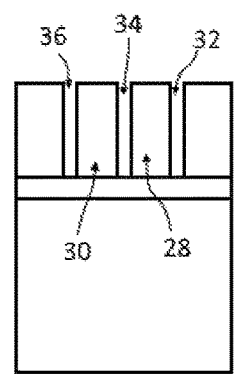
FIG. 2B is a schematic cross-sectional view of the humidity sensor of FIG. 1 taken along line B-B.
Figure 2C:
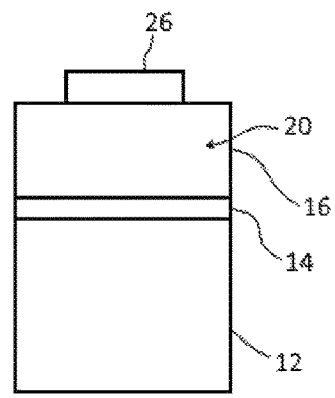
FIG. 2C is a schematic cross-sectional view of the humidity sensor of FIG. 1 taken along line C-C.

FIGS. 1 and 2 depict a trench based capacitive humidity sensor 10 in accordance with one embodiment of the present disclosure. The humidity sensor 10 includes a substrate 12, such as a silicon substrate. An insulating layer 14, such as silicon dioxide, is formed on an upper surface of the substrate 12. A conductive electrode 16 layer is formed on an upper surface of the insulating layer 14. In one embodiment, the substrate 12, insulating layer 14, and electrode layer 16 are implemented by a silicon-on-insulator (SOI). When implemented by an SOI, the electrode layer 16 may comprise a doped silicon layer provided on the insulating layer 14. In alternative embodiments, other substrate types and layer configurations may be utilized. As one alternative, the electrode layer 16 may be implemented by a doped polysilicon layer formed on an insulating layer of a substrate. In another alternative embodiment, the electrode layer 16 may comprise a metal layer deposited onto an insulating layer of a substrate.

As can be seen in FIG. 1, bond pad regions 18, 20 are defined on the surface of the electrode layer 16 for the placement of bond pads 22, 24, 26 that will be used to connect the device to external circuitry (not shown). A first bond pad region 18 is located at a first position on the surface of the electrode layer 16 for receiving bond pads 22, 24 that will be used to connect the capacitor electrodes 28, 30 to readout and control circuitry (not shown).

As depicted in FIG. 1, a pair of trenched electrodes 28, 30 are defined in the electrode layer 16 that will be used to form a capacitor for the humidity sensor 10. A pair of spaced apart bond pads 22, 24 is provided in the first bond pad region 18 for electrically connecting the pair of capacitor electrodes 28, 30 to external circuitry. A first electrically conductive bond pad 22 is positioned over and electrically connected to a first capacitor electrode 22. A second electrically conductive bond pad 24 is positioned over and electrically connected to a second capacitor electrode 30.

A second bond pad region 20 is located at a second position on the surface of the electrode layer 16 for receiving a ground pad or ground contact 26 that will be used to connect the device to ground. The positioning of the bond pad regions 18, 20 and spacing between bond regions depends on a number of factors, such as the materials used, desired capacitor specifications, available space on the substrate, manufacturing techniques, and the like.

A plurality of isolation trenches 32, 34, 36 is formed in the substrate for defining the trenched electrodes 28, 30. As can be seen in FIG. 2, the trenches 32, 34, 36 have substantially vertical sidewalls that reach down to the insulating layer 14 on the substrate 12. The isolation trenches 32, 34, 36 extend horizontally between the bond bad regions 18, 20 and are configured to divide the electrode layer into a plurality of strips to serve as electrode structures for implementing the capacitor for the humidity sensor. The trenches are arranged parallel to each other but can arranged to follow straight, curved, and/or angled paths in the electrode layer.

The number of trenches formed in the substrate depends on the number of electrodes used in the device. In general, two trenches arranged parallel to each other can be used to define a single trenched electrode. To form a pair of adjacent electrodes, a third trench arranged parallel to the first two trenches may be included as depicted in FIG. 1. In the embodiment of FIG. 1, the three trenches 32, 34, 36 are used to define two capacitor electrodes 28, 30 for the humidity sensor 10. The first trench 32 and the second (center) trench 34 are used to define one electrode 28, and the third trench 36 and the second trench 34 are used to define a second electrode 30.

The dimensions of the electrodes 28, 30 for the capacitor depend on the thickness and spacing of the trenches 32, 34, 36 as well as the thickness or depth of the electrode layer 16 which can be controlled to provide electrode structures with predetermined specifications. In one embodiment, the trenches may have an aspect ratio, length to width, between 0.1 µm and 100 µm, and preferably between 1 µm and 10 µm. In one embodiment, the thickness of the electrode layer is between 0.1 µm and 40 µm, and preferably between 2 µm and 15 µm. The isolation trenches may be formed in any suitable manner known in the art that is compatible with the processes and materials used.

As depicted in FIG. 1, the isolation trenches 32, 34, 36 are arranged parallel to each other between the bond pad regions 18, 20. In one embodiment, the isolation trenches 32, 34, 36 are the same size and equally spaced apart from each other so as to define substantially identical electrodes 28, 30 for the capacitor. In alternative embodiments, the widths of the trenches as well as the spacing between trenches and the thickness of the electrode layer may be varied to tailor the characteristics of the device, such as time constants and/or sensing ranges, for specific applications or uses.

As can be seen in FIG. 1, a perimeter isolation trench 38 is formed in the electrode layer 16 of the substrate that connects the first isolation trench 32 to the third isolation trench 36 and defines the outer perimeter of the first bond pad region 18. The second (center) isolation trench 34 extends through the bond pad region 18 and meets the perimeter isolation trench 38 to effectively divide the bond pad region 18 into a first capacitor bond bad region 40 and a second capacitor bond pad region 42. The first bond pad 22 is positioned over and electrically connected to the first electrode 28 in the first capacitor bond pad region 40, and the second bond pad 24 is positioned over and electrically connected to the second electrode 30 in the second capacitor bond pad region 42.

Each trench 32, 34, 36 extends to the ground pad region 20. As can be seen in FIG. 1, a first connection trench 44 connects the ends of the first trench 32 and the second trench 34 in front of the ground pad region 20, and a second connection trench 46 connects the ends of the third trench 36 and the second trench 34 in front of the ground pad region 20. In the embodiment of FIG. 1, the first and second connection trenches 44, 46 form a continuous trench that isolates the capacitor electrodes 28, 30 from the ground pad region 20.

Figure 3:
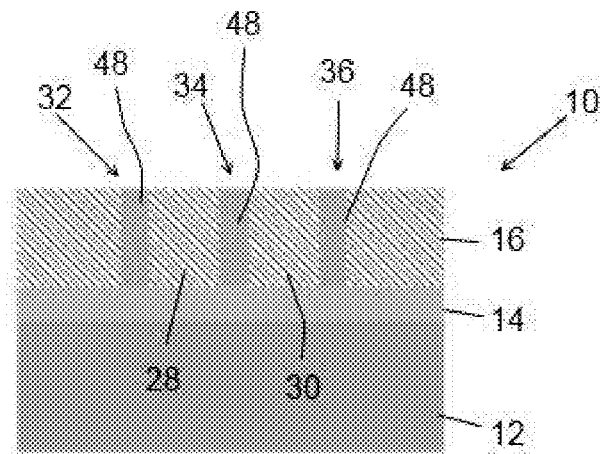
FIG. 3 depicts a cross-sectional view of the humidity sensor of FIG. 1 showing the isolation trenches filled with an insulating material.

After the isolation trenches 32, 34, 36 have been formed in the electrode layer 16 on the substrate 12, an insulating or dielectric material 48 is introduced into the trenches to electrically isolate the electrodes from each other and other components in the substrate. In one embodiment, the insulating material comprises silicon nitride (SiN) as depicted in FIG. 3. In alternative embodiments, any suitable material or combination of materials, including air, may be used as a dielectric material in the trenches.

As depicted in FIG. 3, the insulating material 48 may be introduced into the trenches 32, 34, 36 so as to completely fill each trench. In alternative embodiments, the insulating material may be deposited so that only the sidewalls and bottom of the trenches are covered by the insulating material. After the insulating material has been introduced into the trenches, a planarization or polishing process, such as Chemical Mechanical Polishing (CMP) may be performed to smooth out and flatten the tops of the trenches and upper surface of the electrode layer and make them coplanar.

Figure 4:
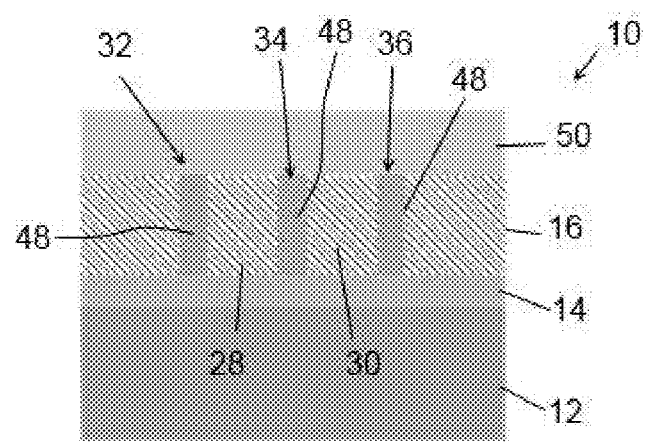
FIG. 4 depicts a cross-sectional view of the humidity sensor of FIG. 1 showing the moisture sensitive dielectric layer deposited onto the electrode layer of the sensor.

After the insulating material 48 has been introduced into the trenches 32, 34, 36 and the upper surface is prepared, a moisture sensitive dielectric layer 50 is deposited over the electrode layer 16 and isolation trenches 32, 34, 36 as depicted in FIG. 4. The dielectric layer 50 is formed of a material having a dielectric constant that changes predictably as a function of relative humidity (e.g., through absorption or adsorption). In one embodiment, the dielectric layer 50 comprises polyimide. A polyimide dielectric layer may be deposited at a thickness of approximately 0.1-50 µm, and preferably at a thickness of approximately 1-20 µm.

In the embodiment of FIGS. 1 and 2, the insulating material in the trenches 32, 34, 36 and on the surface of the electrode layer 16 is intended to limit the passage of electric fields between the electrodes 28, 30 through the trenches 32, 34, 36 and within the depths of the substrate 12. This enables the capacitance measurements to be based at least partially on the stray-fields that pass between the capacitor electrodes through the moisture sensitive dielectric (see, e.g. FIG. 9).

Figure 5:
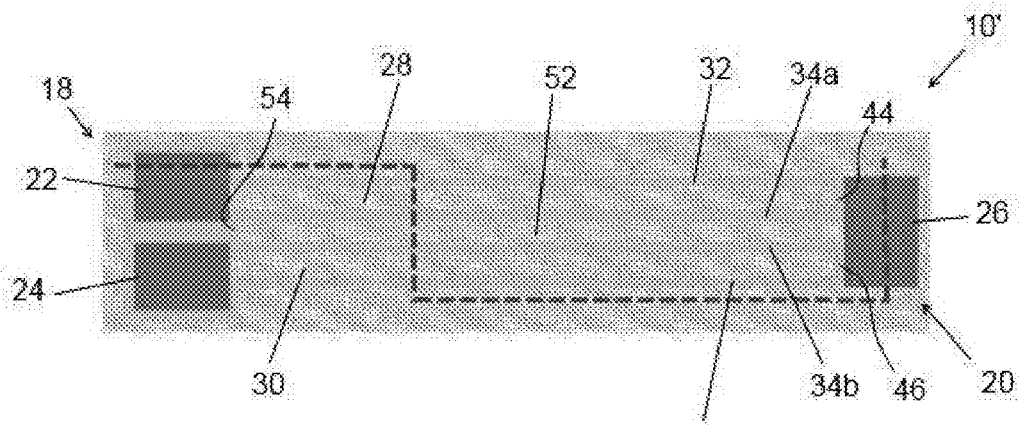
FIG. 5 depicts a top schematic view of another embodiment of a trench based capacitive humidity sensor having a ground electrode interposed between the capacitor electrodes.
Figure 6:
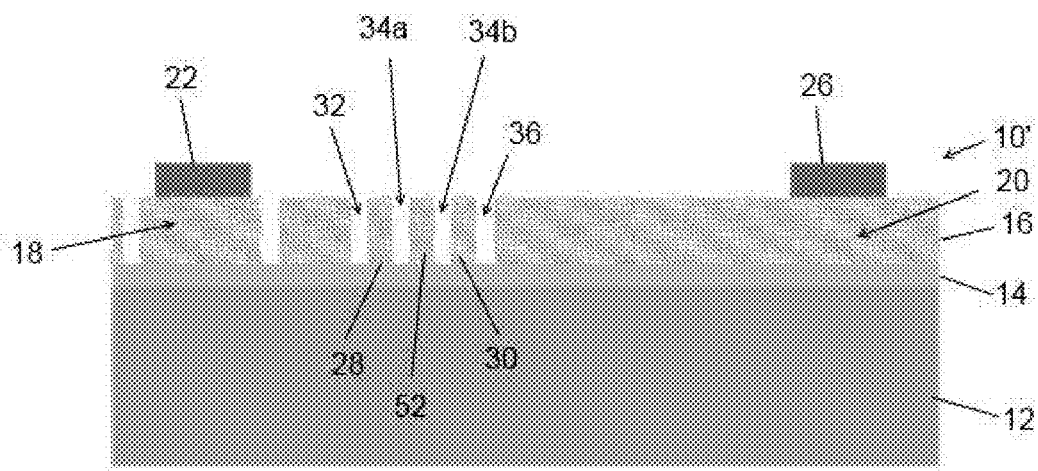
FIG. 6 depicts a side cross-sectional view of the humidity sensor of FIG. 5 taken along the dotted line.

To further improve the isolation of the electrodes 28, 30 within the electrode layer 16, a ground electrode 52 may be provided in the substrate 12 between the capacitor electrodes 28, 30 as depicted in FIGS. 5 and 6. In this embodiment, the humidity sensor 10' has a similar configuration to the sensor of FIGS. 1-4 except for the inclusion of the trenched ground electrode 52 interposed between the two capacitor electrodes 28, 30.

As can be seen in FIGS. 5 and 6, four isolation trenches 32, 34a, 34b, 36 are formed in the electrode layer 16 to define the three electrodes 28, 30, 52. The four trenches are arranged parallel to each other in the electrode layer 16 on the substrate and extend between the first bond pad region 18 and the second bond pad region 20. The first trench 32 and the second trench 34a define the first capacitor electrode 28, the second trench 34a and the third trench 34b define the ground electrode 52, and the third trench 34b and the fourth trench 36 define the second capacitor electrode 30.

In the embodiment of FIGS. 5 and 6, the isolation trenches 32, 34a, 34b, 36 are the same size and equally spaced apart from each other so as to define substantially identically sized capacitor electrodes and ground electrode. In alternative embodiments, the widths of the trenches 32, 34a, 34b, 36 as well as the spacing between trenches and the thickness of the electrode layer may be varied to tailor the characteristics of the device for specific applications or uses.

As depicted in FIG. 5, the first capacitor electrode 28 is electrically connected to the first bond pad 22 and the second capacitor electrode 30 is electrically connected to the second bond pad 24. Near the ground pad region 20, the first trench 32 and the second trench 34a are connected by a connection trench 44 that isolates the first capacitor electrode 28 from the ground pad region 20. Similarly, the fourth trench 36 and the third trench 34b are connected by a connection trench 46 that isolates the second capacitor electrode 30 from the ground pad region 20.

The ends of the second and third trenches 34a, 34b near the ground pad region 20 are spaced apart from each other so that the ground electrode 52 is allowed to extend into the ground pad region 20 where it is electrically connected to the ground pad 26. At the capacitor bond pad region 18, the ends of the second trench 34a and third trench 34b are connected by a connection trench 54 that is positioned to isolate the ground electrode 52 from the capacitor bond pad region 18.

Figure 7:
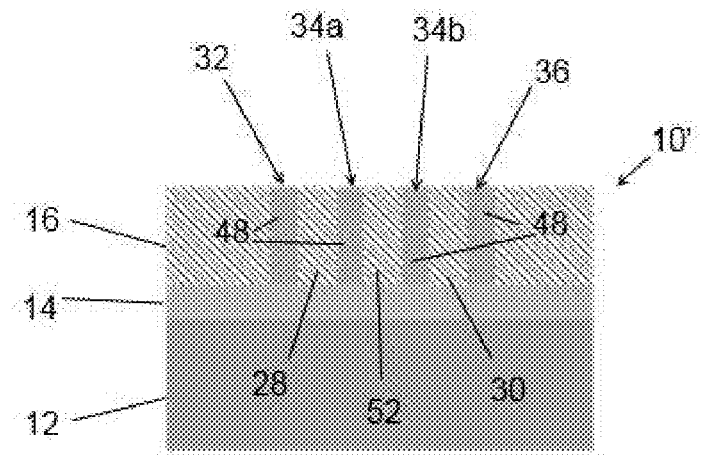
FIG. 7 depicts a cross-sectional view of the humidity sensor of FIG. 5 showing the isolation trenches filled with an insulating material.
Figure 8:
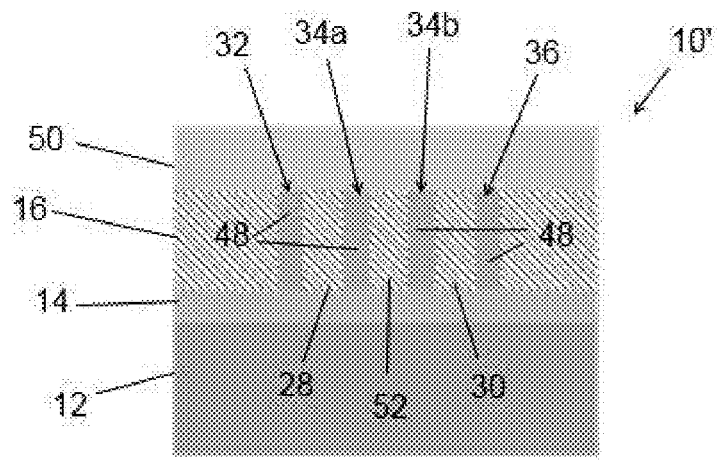
FIG. 8 depicts a cross-sectional view of the humidity sensor of FIG. 5 showing the moisture sensitive dielectric layer deposited onto the electrode layer of the sensor.
Figure 9:
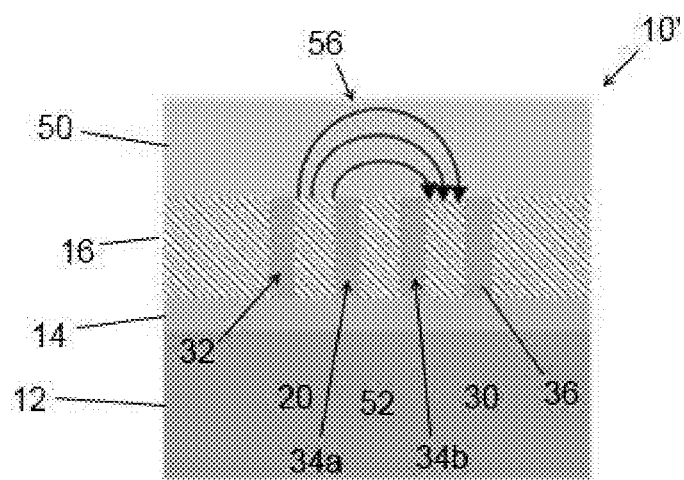
FIG. 9 depicts a cross-sectional view of the humidity sensor of FIG. 5 showing the stray-field lines pass through the moisture sensitive dielectric layer.

The isolation trenches 32, 34a, 34b, 36 may be filled with an insulating material 48, such as SiN, as depicted in FIG. 7. A moisture sensitive dielectric layer 50, such as polyimide, may then deposited over the electrode layer 16 and trenches 32, 34a, 34b, 36 to a desired thickness as depicted in FIG. 8. The ground electrode 52 is configured to enhance isolation of the capacitor electrodes 28, 29 by further preventing the passage of electric fields between the electrodes 28, 30 within the depths of the electrode layer 16 so that capacitance is measured using the stray-field 56 that passes through the moisture-sensitive dielectric 50 as depicted in FIG. 9.

In the embodiment of FIGS. 5-8, each of the capacitor electrodes 28, 30 is connected to a separate bonding pad 22, 24 in order to serve as separate plates of the capacitor, and the ground electrode 52 is connected to a ground pad. In one alternative embodiment, the electrodes 28, 30 may be configured to form an interdigital capacitor electrode structure. For example, the capacitor electrodes 28, 30 may be electrically connected to each other, e.g., by omitting the isolation trench between the two capacitor bond pad regions or by electrically connecting the first and third electrodes 28, 30 to the same bond pad (not shown). The electrodes 28, 30 are then configured to serve as a single capacitor electrode. The ground electrode 52 may then be configured to serve as the second capacitor electrode by connecting the bond pad 26 to appropriate circuitry rather than to ground.

Figure 10:
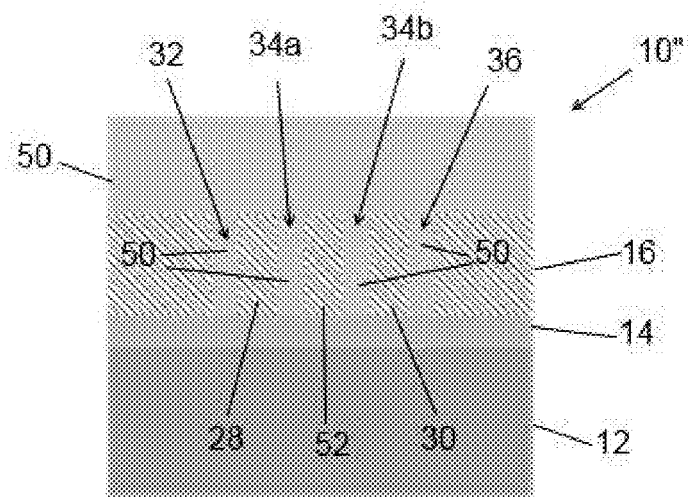
FIG. 10 depicts a cross-sectional view of another embodiment of a trench based capacitive humidity sensor in which the trenches are filled with the moisture sensitive dielectric material.

As described above, a dielectric insulation material, such as SiN, may be introduced into the trenches in order to increase electric field coupling through the moisture sensitive dielectric layer on top of the electrodes and trenches. In an alternative embodiment, the trenches may be filled with the same moisture sensitive dielectric material that is used to cover the electrode layer and trenches so that capacitive coupling may occur through the trenches as well as through the PI coating layer. For example, referring to FIG. 10, an embodiment of a trench based capacitive humidity sensor 10" is depicted in which the isolation trenches 32, 34a, 34b, 36 between electrodes 28, 52, 30 are completely filled with a moisture sensitive dielectric material 50, such as polyimide, in addition to the moisture sensitive dielectric layer 50 layer or coating provided on top of the electrode layer 16.

Figure 11:
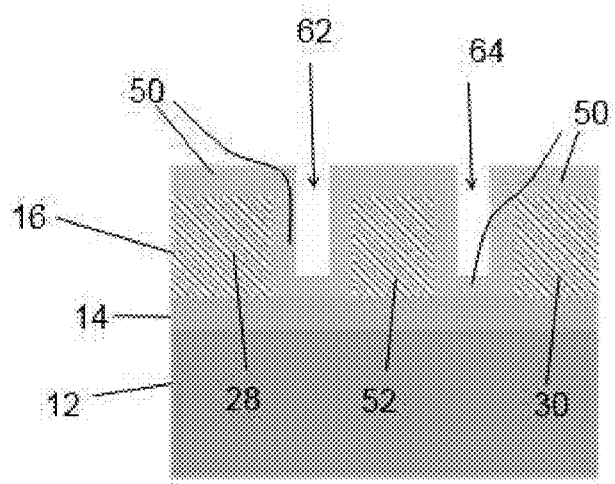
FIG. 11 depicts a cross-sectional view of another embodiment of a trench based capacitive humidity sensor in which the trench walls are covered with a thin layer of moisture sensitive dielectric material.

As an alternative to completely filling the trenches with the insulating material, the trenches may be lined with a thin layer of the material so that only the sidewalls and bottom of the trenches are covered and the central portions of the trenches are unfilled as depicted in FIG. 11. The thickness of the polyimide layer 50 covering the electrode layer 16 and walls of the trenches can be varied to alter the time constant or sensing ranges of the sensor. In the embodiment of FIG. 11, two trenches 62, 64 are used to divide the electrode layer 16 into the three electrodes. The electrodes 28, 30 extend to the lateral edges of the device. In one embodiment, the electrodes 28, 30 are configured as separate capacitor electrodes, and the central electrode 52 is connected as a ground electrode. In an alternative embodiment, the electrodes 28, 30 are connected together to form a single capacitor electrode and the electrode 52 is connected as a second capacitor electrode.

The devices above are described as having two electrodes 28, 30 for implementing a single capacitive device with the possible inclusion of a ground electrode for maximizing the stray-field in the moisture sensitive film. In some embodiments, additional trenched capacitor electrodes may be formed in the substrate to implement multiple capacitors in the same device. The dimensions of the trenches may be varied to provide multiple possible capacitive couplings with different time constants, sensitivities, and sensing ranges in a single element.

Figure 12:
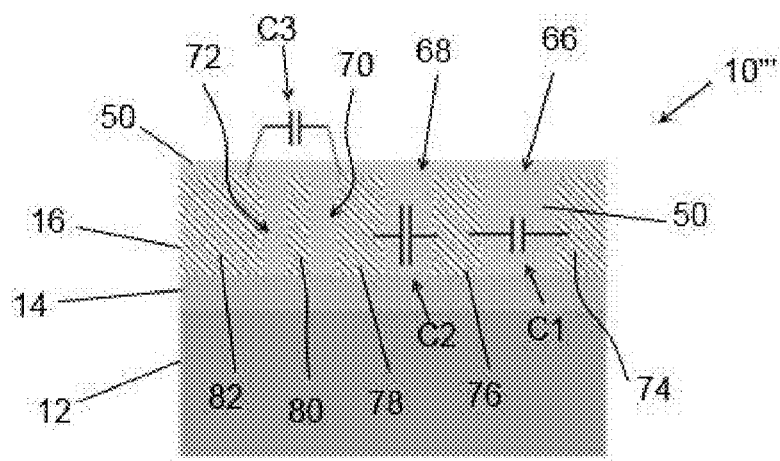
FIG. 12 depicts a cross-sectional view of another embodiment of a trench based capacitive humidity sensor in which isolation trenches define electrodes for multiple capacitors with varying dimensions.

An example of a trench based capacitive humidity sensor 10''' with multiple capacitors is depicted in FIG. 12. The trenches are filled with a moisture sensitive dielectric 50, such as polyimide, with a relatively thin layer or coating of the moisture sensitive material 50 being provided over the top of the electrode layer so that capacitive coupling occurs primarily through the trenches. This configuration enables the trench widths to be used to set the performance characteristics of each capacitor implemented in the device. By varying the width of the trenches between the electrodes, multiple capacitors can be provided in the same chip with different time constants, sensitivities, and/or sensing ranges.

In the embodiment of FIG. 12, four isolation trenches 66, 68, 70, 72 are formed in the electrode layer 16 of the substrate 12 that form five trenched electrodes 74, 76, 78, 80, 82. The first electrode 74 and the second electrode 76 are configured to implement a first capacitor C1. The second electrode 76 and the third electrode 78 are configured to implement a second capacitor C2. The third, fourth, and fifth electrodes 78, 80, 82 are configured to implement a third capacitor C3. The third capacitor C3 is configured as interdigital electrode capacitor with the third and fifth electrodes 78, 82 serving as capacitor electrodes and the fourth electrode 80 serving as a ground electrode between the capacitor electrodes.

The first isolation trench 66 separates the first capacitor electrode 74 and the second capacitor electrode 76 and has a width that is wider than the second isolation trench 68 that separates the second capacitor electrode 76 and the third capacitor electrode 78. As a result, the first capacitor C1 has different performance characteristics than the second capacitor C2, such as a longer time constant for example. Due to the third capacitor C3 having an interdigital configuration with a ground electrode 80 interposed between the capacitor electrodes 78, 82, the capacitance between the capacitor electrodes 78, 82 is based primarily on the stray-field that extends over the ground electrode 80 and passes through the upper layer of moisture sensitive dielectric 50 (and possibly the air). This enables the third capacitor C3 to have different performance characteristics than the first and second capacitors, such as increased sensitivity for example.

Because the capacitive humidity sensors described above are based on trenched conductive layers on conventional substrates, the capacitive humidity sensors can be easily fabricated using CMOS processes as part of normal CMOS flow. As a result, the capacitive humidity sensor can be easily integrated onto the same chip with other sensors, such as capacitive sensors and microphones. Functional integration of capacitive humidity sensors into other sensor devices enables a significant reduction in cost as the same application specific integrated circuit (ASIC), same MEMS process, and same packaging may be used. Thus, humidity sensing functionality may be added to other sensors and devices at almost no additional cost.

CMOS integration also enables other features for the humidity sensor to be implemented using CMOS. For example, a heating structure (not shown), such as a resistive heating element, may easily be incorporated into the substrate beneath or alongside the humidity sensors. The heating structure can be used to generate heat to increase the speed of desorption of absorbed or adsorbed moisture from the moisture sensitive dielectric.

Figure 13:
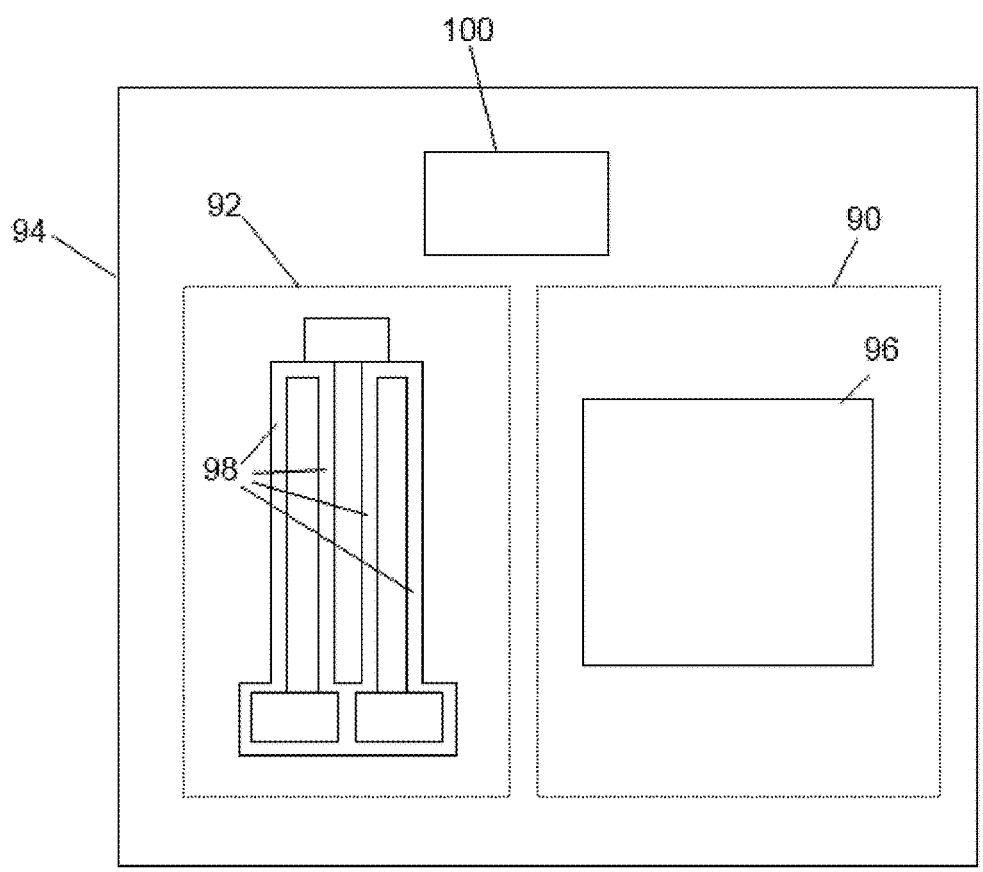
FIG. 13 is a schematic view of a trench based capacitive humidity sensor integrated into a MEMS pressures sensor.

As an example, a schematic depiction of a device is depicted in FIG. 13 that includes a MEMS capacitive pressure sensor 90 and a trench based capacitive humidity sensor 92 implemented on the same chip 94. In one embodiment, the pressure sensor 90 is fabricated on a substrate using a CMOS process in which the fixed electrode (not shown) for the pressure sensor is implemented in the substrate and a movable electrode (96) is implemented in an upper layer, e.g., polysilicon, above the fixed electrode. The fixed electrode and movable electrode are separated by a sacrificial layer (not shown), e.g., silicon dioxide, that is removed to release the movable electrode (which forms a flexible membrane) and form a capacitive gap between the electrodes.

The trench based humidity sensor 92 is implemented in the same substrate alongside the MEMS pressure sensor in accordance with the embodiments described above, and may be implemented in the same layer stack as the pressure sensor 90. For example, the trenches 98 for the humidity sensor may be formed in the polysilicon layer of the substrate. In addition, the ASIC 100 for the MEMS pressure sensor 90 may be configured, e.g., in multiplex (MUX) mode, to control the operation and readout of the humidity sensor.

While the disclosure has been illustrated and described in detail in the drawings and foregoing description, the same should be considered as illustrative and not restrictive in character. It is understood that only the preferred embodiments have been presented and that all changes, modifications and further applications that come within the spirit of the disclosure are desired to be protected.

What is claimed is:

1. A sensor device comprising:
   a silicon-on-insulator (SOI) including a silicon substrate, an insulating layer on the silicon substrate, and a silicon layer on the insulating layer;
   a plurality of trenches defined in the silicon layer that extend down to the insulating layer, the plurality of trenches surrounding and isolating two strips in the silicon layer from each other and from the rest of the silicon layer, the two strips being arranged substantially parallel to each other and extending between a first region and a second region of the silicon layer and configured to implement a first and a second capacitor electrode of a first capacitor;
   an insulating material that fills each of the trenches the plurality of trenches; and
   a moisture sensitive dielectric layer on the silicon layer extending over the plurality of trenches filled with the insulating material, the moisture sensitive dielectric layer being in contact with the insulating material in the trenches and in contact with the silicon layer between the trenches, the moisture sensitive dielectric layer having a dielectric constant that changes as a function of relative humidity,
   wherein the plurality of trenches are completely filled with the insulating material,
   wherein the moisture sensitive dielectric layer is polyimide, and
   wherein the insulating material received in the trenches is silicon nitride.

2. The device of claim 1, wherein polyimide layer is deposited to a thickness of approximately 0.1-50 μm.

3. The device of claim 2, wherein the polyimide layer is layer is deposited to a thickness of approximately 1-20 μm.

4. The device of claim 1, further comprising:
   a first bond pad electrically connected to the first capacitor electrode in the first region; and
   a second bond pad electrically connected to the second capacitor electrode in the second region.

5. The device of claim 4, wherein the plurality of trenches defines a third strip in the silicon layer arranged between and isolated from the first capacitor electrode and the second capacitor electrode, the third strip being configured as a ground electrode, and
   wherein the ground electrode is electrically connected to a third bond pad.

6. The device of claim 1, wherein the plurality of trenches defines a third strip in the silicon layer that is arranged parallel to and isolated from the second capacitor electrode, the third strip being configured as a third capacitor electrode, the third capacitor electrode and the second capacitor electrode forming a second capacitor.

7. The device of claim 6, wherein a first trench longitudinally separates the first capacitor electrode from the second capacitor electrode, the first trench having a first width, and wherein a second trench separates the second capacitor electrode from the third capacitor electrode, the second trench having a second width that is different than the first width.

\* \* \* \* \*